United States Patent [19]

Fischer, deceased et al.

[11] 4,009,192
[45] Feb. 22, 1977

[54] O-AMINOSULFONYLGLYCOLIC AMIDES

[75] Inventors: Adolf Fischer, deceased, late of Mutterstadt, Germany, by Caecilia Emma Fischer, heiress-at-law; Hanspeter Hansen, Ludwigshafen; Wolfgang Rohr, Mannheim, both of Germany

[73] Assignee: BASF Aktiengesellschaft, Ludwigshafen (Rhine), Germany

[22] Filed: June 16, 1975

[21] Appl. No.: 587,355

[30] Foreign Application Priority Data

July 1, 1974 Germany .......................... 2431582

[52] U.S. Cl. .............................. 260/456 A; 71/103; 260/561 HL; 260/561 B; 260/490
[51] Int. Cl.² ........................................ C07C 143/68
[58] Field of Search ................................ 260/456 A

[56] References Cited

UNITED STATES PATENTS

| | | | |
|---|---|---|---|
| 3,536,721 | 10/1970 | Soong et al. | 260/456 A |
| 3,865,860 | 2/1975 | Rohr et al. | 260/456 A |
| 3,870,740 | 3/1975 | Fischer et al. | 260/456 A |

Primary Examiner—James O. Thomas, Jr.
Assistant Examiner—Nicky Chan
Attorney, Agent, or Firm—Johnston, Keil, Thompson & Shurtleff

[57] ABSTRACT

New, substituted O-(aminosulfonyl)-glycolic amides having a strong herbicidal action, herbicides containing these active ingredients, a process for controlling the growth of unwanted plants with these compounds, and a process for producing these compounds.

13 Claims, No Drawings

O-AMINOSULFONYLGLYCOLIC AMIDES

The present invention relates to new and valuable substituted O-(aminosulfonyl)-glycolic amides, their manufacture, herbicides containing these compounds, and their use as herbicides.

The use of N,N-diallyl-2-chloroacetamide (German Printed Application DAS 1,014,380) and O-(isopropylaminosulfonyl)-glycolic acid-N-butyn-1-yl anilide (German Laid-Open Application DOS 2,201,432) as selective herbicides in various crops is known.

The object of the invention is to provide herbicides which cause greater damage to unwanted plants than prior art herbicides applied at the same rate - the unwanted plants can be completely destroyed with a small amount of active ingredient. As a result, damage to crop plants likely to be caused by higher application rates is avoided, and residues in both plant and soil are reduced.

We have now found that substituted O-(aminosulfonyl)-glycolic amides of the formula

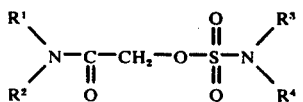

where $R^1$ and $R^2$ each denote unsubstituted or halogen-substituted alkyl of 1 to 8 carbon atoms, alkenyl of 3 to 8 carbon atoms, alkynyl of 3 to 8 carbon atoms, or cycloalkyl of a maximum of 3 to 8 carbon atoms, and $R^3$ and $R^4$ each denote hydrogen, unsubstituted or halogen-substituted alkyl of 1 to 8 carbon atoms, alkenyl of 3 to 8 carbon atoms, alkynyl of 3 to 8 carbon atoms, or cycloalkyl of a maximum of 8 carbon atoms, have an excellent herbicidal action and good crop plant compatibility.

$R^1$ and $R^2$ may for instance be linear or branched, unsubstituted or halogen (especially fluoro, chloro and bromo)-substituted alkyl, alkenyl, alkynyl and cycloalkyl. Preferred radicals are alkyl of 1 to 8 carbon atoms, for example methyl, ethyl, n-propyl, isopropyl, n-butyl, isobutyl, sec-butyl, tert-butyl, pentyl-1, 2-methylbutyl-3, pentyl-3, hexyl, 2-methylpentyl-3, 3-methylpentyl-4, heptyl, octyl, chloromethyl, 2-chloroethyl, and 2-fluoroethyl, alkenyl of 3 to 8 carbon atoms, for instance allyl, butenyl, pentenyl, hexenyl, heptenyl, and octenyl, alkynyl of 3 to 8 carbon atoms, for example propargyl, butynyl, pentynyl, hexynyl, heptynyl, and octynyl, and cycloalkyl, for instance cyclopentyl, cyclohexyl, cycloheptyl and cyclooctyl.

$R^3$ and $R^4$ may be hydrogen, linear or branched, unsubstituted or halogen (especially fluoro, chloro and bromo)-substituted alkyl, alkenyl, alkynyl and cycloalkyl. Preferred radicals are alkyl of 1 to 8 carbons atoms, for example methyl, ethyl, n-propyl, isopropyl, n-butyl, isobutyl, sec-butyl, tert-butyl, pentyl-1, 2-methylbutyl-3, pentyl-3, hexyl, 2-methylpentyl-3, 3-methylpentyl-4, heptyl, octyl, 2-chloroethyl, and 2-fluoroethyl, alkenyl of 3 to 8 carbon atoms, for instance allyl, butenyl, pentenyl, hexenyl, heptenyl, and octenyl, alkynyl of 3 to 8 carbon atoms, for example propargyl, butynyl, pentynyl, hexynyl, heptynyl, and octynyl, and cycloalkyl, for instance cyclopentyl, cyclohexyl, cycloheptyl and cyclooctyl. The precipitated hydrochloride may also be separated from the organic phase by suction filtration.

The new O-(aminosulfonyl)-glycolic amides may be prepared from a glycolic amide and an aminosulfonyl halide in accordance with the following equation:

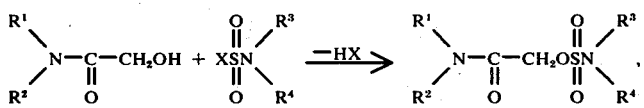

$R^1$, $R^2$, $R^3$ and $R^4$ having the above meanings and X denoting chloro or bromo. This reaction is preferably carried out in the presence of an acid-binding agent, e.g., a tertiary amine such as pyridine and triethylamine, or after addition of an aqueous solution of an inorganic base (alkali metal or alkaline earth metal hydroxides).

Expediently, approximately equimolar amounts of glycolic amide and aminosulfonyl halide are reacted in an inert solvent in the presence of an acid acceptor at a temperature of from 0° to 30°, preferably 0° to 10°C. Examples of suitable solvents are dichloromethane, benzene, toluene, chloroform, ethers such as dialkyl ether and cyclic ethers, and cyclohexane. If the amount of amine, e.g., pyridine, is in excess of that necessary as an acid acceptor, this excess may replace the solvent. The organic reaction mixture is expediently worked up by washing it successively with water, dilute hydrochloric acid, water and a weakly alkaline aqueous solution, e.g., sodium bicarbonate solution. Subsequently, the organic phase is dried with a suitable agent, e.g., sodium sulfate and magnesium sulfate, and concentrated in vacuo. The residue is recrystallized from a suitable solvent, e.g., diethyl ether.

EXAMPLE 1

At 0° to 5° C and while stirring, a soluton of 24.4 parts by weight of methylaminosulfonyl chloride (approx. 90%) in 40 parts by weight of dichloromethane was metered into a solution of 23.25 parts by weight of glycolic acid-N,N-diallyl amide and 17.2 parts by weight of triethylamine in 100 parts by weight of dichloromethane.

The reaction mixture was then washed successively with water, dilute hydrochloric acid, water, and dilute aqueous sodium bicarbonate solution. The organic phase was dried with magnesium sulfate and concentrated in vacuo. The residue was recrystallized from diethyl ether; m.p.: 47° C.

The compound has the following structural formula:

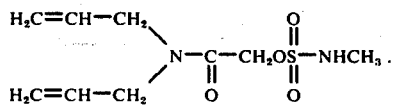

The following compounds were prepared analogously:

| R¹ | R² | R³ | R⁴ | |
|---|---|---|---|---|
| CH₂=CH—CH₂ | CH₂=CH—CH₂ | H | H | 96 – 97 |
| CH₂=CH—CH₂ | CH₂=CH—CH₂ | C₂H₅ | H | 40 – 41 |
| CH₂=CH—CH₂ | CH₂=CH—CH₂ | n-C₃H₇ | H | 1.4865 |
| CH₂=CH—CH₂ | CH₂=CH—CH₂ | i-C₃H₇ | H | 38 – 40 |
| CH₂=CH—CH₂ | CH₂=CH—CH₂ | C₄H₉ | H | 1.4840 |
| CH₂=CH—CH₂ | CH₂=CH—CH₂ | sec-C₄H₉ | H | 34 – 36 |
| CH₂=CH—CH₂ | CH₂=CH—CH₂ | ClCH₂CH₂ | H | 77 – 78 |
| CH₂=CH—CH₂ | CH₂=CH—CH₂ | CH₃ | CH₃ | 1.4830 |
| CH₂=CH—CH₂ | CH₂=CH—CH₂ | C₂H₅ | C₂H₅ | 1.4800 |
| CH₂=CH—CH₂ | CH₂=CH—CH₂ | CH₃ | C₂H₅ | 1.4812 |
| CH₂=CH—CH₂ | CH₂=CH—CH₂ | ClCH₂CH₂ | CH₃ | 1.4960 |
| CH₂=CH—CH₂ | CH₂=CH—CH₂ | CH₂=CH—CH₂ | CH₃ | |
| CH₂=CH—CH₂ | CH₂=CH—CH₂ | CH≡C—CH₂ | CH₃ | |
| C₂H₅ | C₂H₅ | CH₃ | H | |
| C₂H₅ | C₂H₅ | C₂H₅ | H | |
| C₂H₅ | C₂H₅ | n-C₃H₇ | H | |
| C₂H₅ | C₂H₅ | i-C₃H₇ | H | 74 – 75 |
| C₂H₅ | C₂H₅ | n-C₄H₉ | H | |
| C₂H₅ | C₂H₅ | CH₃ | CH₃ | |
| sec-C₄H₉ | sec-C₄H₉ | H | H | |
| sec-C₄H₉ | sec-C₄H₉ | n-CH₃ | H | |
| sec-C₄H₉ | sec-C₄H₉ | C₂H₅ | H | |
| sec-C₄H₉ | sec-C₄H₉ | n-C₃H₇ | H | |
| sec-C₄H₉ | sec-C₄H₉ | i-C₃H₇ | H | 55 – 57 |
| sec-C₄H₉ | sec-C₄H₉ | n-C₄H₉ | H | |
| sec-C₄H₉ | sec-C₄H₉ | sec-C₄H₉ | H | |
| sec-C₄H₉ | sec-C₄H₉ | ClCH₂—CH₂ | H | |
| sec-C₄H₉ | sec-C₄H₉ | CH₃ | CH₃ | |
| sec-C₄H₉ | sec-C₄H₉ | C₂H₅ | C₂H₅ | |
| i-C₃H₇ | i-C₃H₇ | H | H | |
| i-C₃H₇ | i-C₃H₇ | CH₃ | H | 86 – 87 |
| i-C₃H₇ | i-C₃H₇ | C₂H₅ | H | |
| i-C₃H₇ | i-C₃H₇ | n-C₃H₇ | H | |
| i-C₃H₇ | i-C₃H₇ | i-C₃H₇ | H | 73 – 74 |
| i-C₃H₇ | i-C₃H₇ | C₄H₉ | H | |
| i-C₃H₇ | i-C₃H₇ | sec-C₄H₉ | H | |
| i-C₃H₇ | i-C₃H₇ | ClCH₂CH₂ | H | 88 – 90 |
| i-C₃H₇ | i-C₃H₇ | CH₃ | CH₃ | |
| i-C₃H₇ | i-C₃H₇ | C₂H₅ | C₂H₅ | |
| CH₃ | CH≡C—CH(CH₃) | H | H | |
| CH₃ | CH≡C—CH(CH₃) | CH₃ | H | 80 – 81 |
| CH₃ | CH≡C—CH(CH₃) | C₂H₅ | H | 46 – 48 |
| CH₃ | CH≡C—CH(CH₃) | n-C₃H₇ | H | 104 – 105 |
| CH₃ | CH≡C—CH(CH₃) | i-C₃H₇ | H | 87 – 88 |
| CH₃ | CH≡C—CH(CH₃) | n-C₄H₉ | H | |
| CH₃ | CH≡C—CH(CH₃) | sec-C₄H₉ | H | |
| CH₃ | CH≡C—CH(CH₃) | ClCH₂CH₂ | H | 96 – 97 |
| CH₃ | CH≡C—CH(CH₃) | CH₃ | CH₃ | |
| CH₃ | CH≡C—CH(CH₃) | C₂H₅ | C₂H₅ | |
| CH₃ | CH₃ | H | H | |
| CH₃ | CH₃ | CH₃ | H | |
| CH₃ | CH₃ | C₂H₅ | H | |
| CH₃ | CH₃ | n-C₃H₇ | H | |
| CH₃ | CH₃ | i-C₃H₇ | H | |
| CH₃ | CH₃ | n-C₄H₉ | H | |
| CH₃ | CH₃ | sec-C₄H₉ | H | |
| CH₃ | CH₃ | ClCH₂ | H | |
| CH₃ | CH₃ | CH₃ | CH₃ | |
| CH₃ | CH₃ | C₂H₅ | C₂H₅ | |
| C₂H₅ | i-C₃H₇ | H | H | |
| C₂H₅ | i-C₃H₇ | CH₃ | H | |
| C₂H₅ | i-C₃H₇ | C₂H₅ | H | |
| C₂H₅ | i-C₃H₇ | C₃H₇ | H | |
| C₂H₅ | i-C₃H₇ | i-C₃H₇ | H | |
| C₂H₅ | i-C₃H₇ | n-C₄H₉ | H | |
| C₂H₅ | i-C₃H₇ | sec-C₄H₉ | H | |
| C₂H₅ | i-C₃H₇ | ClCH₂CH₂ | H | |
| C₂H₅ | i-C₃H₇ | CH₃ | CH₃ | |
| C₂H₅ | i-C₃H₇ | C₂H₅ | C₂H₅ | |
| n-C₃H₇ | HC≡C—CH₂ | C₂H₅ | H | 1.4855 |
| n-C₃H₇ | HC≡C—CH₂ | i-C₃H₇ | H | 55 – 58 |
| n-C₃H₇ | HC≡C—CH₂ | ClCH₂CH₂ | H | 76 – 79 |
| i-C₃H₇ | HC≡C—CH₂ | C₂H₅ | H | |
| i-C₃H₇ | HC≡C—CH₂ | i-C₃H₇ | H | |

The glycolic amides used as starting materials may be prepared analogously to the process described in J. Chem. Soc., 1357, 1951, by reaction of 1,3-dioxolane-2,4-dione with suitable secondary aliphatic amines, as illustrated below.

At 20° to 25° C and while stirring, a solution of 158 parts by weight of 1,3-dioxolane-2,4-dione in 230 parts by weight of tetrahydrofuran was metered as carbon dioxide evolved into a solution of 150 parts by weight of diallylamine in 330 parts by weight of tetrahydrofuran. When no more gas evolved the mixture was freed from solvent in vacuo and the residue then distilled; b.p. (0.01 mm): 85° C; $n_D^{25}$: 1.4855.

The compound, N,N-diallylglycolic amide, has the following structural formula:

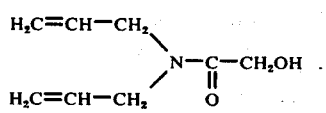

The glycolic amides may also be obtained by the following routes:

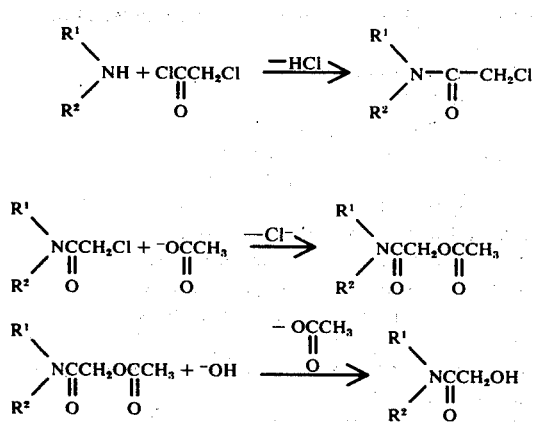

The acetoxyacetamides obtained as intermediates may also be prepared direct by reacting acetoxyacetyl chloride with secondary amines in the presence of an acid acceptor in accordance with the following equation:

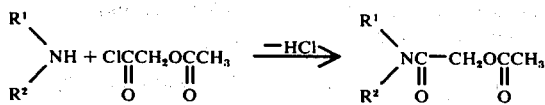

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agents and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts or sulfated fatty alcohol glycol ether, condensation products of sulfonated naphthalene and naphthalene derivatives with formaldehyde, condensation products of naphthalene or naphthalenesulfonic acids with phenol and formaldehyde, polyoxymethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders. etc.

The formulations contain from 0.1 to 95, and preferably 0.5 to 90%, by weight of active ingredient.

There may be added to the compositions or individual active ingredients (if desired, immediately before use (tankmix)) oils of various types, wetting agents or adherents, herbicides, fungicides, nematocides, insecticides, bactericides, trace elements, fertilizers, antifoams (e.g., silicones), growth regulators, antidotes and other herbicidally effective compounds such as
substituted alkylsulfonylglycolic amides and imides
  substituted alkylaminosulfonylglycolic amides and
  imides substituted acetanilidoalkyl sulfites substituted anilines substituted azides
substituted aryloxycarboxylic acids and aryloxythiocarboxylic acids and salts, esters and amides thereof,
substituted alkanols, alkenols
substituted ethers
substituted arsonic acids and arsenic acids and salts, esters and amides thereof
substituted benzene sulfonamides substituted benzimidazoles
substituted benzisothiazoles
substituted dihydrobenzofuranyl alkylamino sulfonates
substituted benzothiadiazinone dioxides
substituted benzoxazines
substituted benzoxazinones
substituted benzoxazoline thiones
substituted benzothiadiazoles
substituted benzothiazolinyl alkyl carboxylic acids and salts, esters and amides thereof
substituted biurets
substituted quinolines
substituted carbamates
substituted aliphatic or cycloaliphatic carboxylic acids and thiocarboxylic acids and their salts, esters and amides
substituted aromatic carboxylic acids and thiocarboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzeofuranyl sulfonates
substituted dihydropyran diones
substituted disulfides
substituted dioxanes
substituted dipyridylium salts
substituted dithiocarbamates
substituted dithiophosphoric acids and their salts, esters and amides
substituted fluoroenecarboxylic acids and their salts, esters and amides
substituted ureas
substituted hexahydro-1H-carbothioates
substituted hydantoins
substituted hydrazides
substituted hydrazonium salts
substituted hydrofuranones
substituted isoxazole pyrimidones
substituted imidazoles
substituted imidazolidinedione carboxamides
substituted isothiazole pyrimidones
substituted ketones
substituted naphthoquinones
substituted naphthalic anhydrides
substituted aliphatic nitriles
substituted aromatic nitriles
substituted oxadiazoles
substituted oxadiazinones
substituted oxadiazolines
substituted oxadiazolidine diones
substituted oxazolidines
substituted oxadiazine diones
substituted oxazole pyrimidinones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted sulfamates
substituted styrenes
substituted sulfonyl toluidides
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiobenzamides
substituted thiocarboxylic acids and their salts, esters and amides
substituted thiol carbamates
substituted thioureas
substituted thiophosphoric acids and their salts, esters and amides
substituted triazines
substituted triazinones
substituted triazoles
substituted uracils
substituted uretidine diones chlorates, and
substituted azetidine carbothioates.

The last-mentioned herbicidal compunds may also be applied before or after the active ingredients or compositions thereof according to the invention.

These agents may be added to the herbicides according to the invention in a ratio by weight of from 1:10 to 10:1. The same applies to oils, wetting agents and adherents, fungicides, nematocides, insecticides, bactericides, antidotes and growth regulators.

The agents of the invention may be used once or several times before or after planting, before sowing, and before, during or after emergence of the crop plants and unwanted plants.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
etc.;
cyperaceae, such as
    Carex spp.
    Cyperus spp.
    etc.;
dicotyledonousweeds, such as
    Malvaceae, e.g.,
        Abutilon theoprasti
        Sida spp.
        etc.;
    Ambrosia spp.
    Lactuca spp.
    Senecio spp.
    Sonchus spp.
    Xanthium spp.
    Iva spp.
    Galinsoga spp.
    Taraxacum spp.
    Chrysanthemum spp.
    Cirsium spp.
Convolvulaceae, such as
    Convolvulus spp.
    Ipomoea spp.
    etc.;
Cruciferae, such as
    Barbarea vulgaris
    Brassica spp.
    Capsella spp.
    Sisymbrium spp.
    Thlaspi spp.
    Sinapis arvensis
    etc.;
Geraniaceae, such as
    Erodium spp.
    etc.;
Portulacaceae, such as
    Portulaca spp.
Primulaceae, such as
    Anagallis arvensis
    etc.;
Rubiaceae, such as
    Richardia spp.
    Galium spp.
Scrophulariaceae, such as
    Linaria spp.
    Veronica spp.
Solanaceae, such as
    Physalis spp.
    Solanum spp.
    etc.;
Urticaceae, such as
    Urtica spp.
Violaceae, such as
    Viola spp.
Zygophyllaceae, such as
    Tribulus terrestris
Euphorbiaceae, such as
    Mercurialis annua
Umbelliferae, such as
    Daucus carota
    Aethusa cynapium
Commelinaeae, such as
    Commelina spp.
Labiatae, such as
    Lamium spp.
    etc.;
Leguminosae, such as
    Medicago spp.
    Trifolium spp.
    Vicia spp.
    etc.;
Plantaginaceae, such as
    Plantago spp.
Polygonaceae, such as
    Polygonum spp.
    Rumex spp.
Aizoaceae, such as
    Mollugo verticillata
Amaranthaceae, such as
    Amaranthus spp.
Boraginaceae, such as
    Amsinckia spp.

Dactylis spp.
Avena spp.
Bromus spp.
Uniola spp.
Poa
Leptochloa spp.
Brachiaria spp.
Eleusine spp.
Cenchrus spp.
Eragrostis spp.
Phragmitres communis Eleocharis spp.
Scirpus spp.

Hibiscus spp.
Malva spp.
Compositae, such as
    Centaurea spp.
    Tussilago spp.
    Lapsana communis
    Tagetes spp.
    Erigeron spp.
    Anthemis spp.
    Matricaria spp.
    Artemisia spp.
    Bidens spp.
    etc.;

Cuscuta spp.
Jaquemontia tamnifolia

Arabidopsis thaliana
Descurainia spp.
Draba spp.
Coronopus didymus
Lepidium spp.
Raphanus spp.

Geranium spp.

etc.;

Lysimachia spp.

Diodia spp.
etc.;

Digitalis spp.
etc.;

Nicandra spp.
Datura spp.

etc.;

etc.;

Euphorbia spp.

Ammi majus
etc.;

etc.;

Galeopsis spp.

Sesbania exaltata
Cassia spp.
Lathyrus spp.

etc.;

Fagopyrum spp.
etc.;

etc.;

etc.;

Anchusa spp.

*-continued*

Myostis spp.
etc.;
Caryophyllaceae, such as
    Stellaria spp.
    Spergula spp.
    Saponaria spp.
    Scleranthus annuus
Chenopodiaceae, such as
    Chenopodium spp.
    Kochia spp.
    Salsola Kali
Lythraceae, such as
    Cuphea spp.
Oxalidaceae, such as
    Oxalis spp.
Ranunculaceae, such as
    Ranunculus spp.
    Delphinium spp.
Papaveraceae, such as
    Papaver spp.
    etc.;
Onagraceae, such as
    Jussiaea spp.
Rosaceae, such as
    Alchemillia spp.
    etc.;
Potamogetonaceae, such as
    Potamogeton spp.
Najadaceae, such as
    Najas spp.
Equisetaceae
    Equisetum spp.
Marsileaceae, such as
    Marsilea quadrifolia
Polypodiaceae,
    Pteridium quilinum
Alismataceae, such as
    Alisma spp.
    etc.

Lithospermum spp.

Silene spp.
Cerastium spp.
Agrostemma githago
etc.;

Atriplex spp.
Monolepsis nuttalliana
etc.;

etc.;

Adonis spp.
etc.;

Fumaria officinalis etc.;

Potentilla spp.

etc.;

etc.;

etc.;

etc.;

Sagittaria sagittifolia

The amount used of the agents of the invention may vary and depends on the effect desired; it generally is from 0.1 to 15 or more, and preferably from 0.2 to 6, kg per hectare.

The herbicides according to the invention may be employed in cereal crops such as

| | |
|---|---|
| Avena spp. | Sorghum |
| Triticum spp. | Zea mays |
| Hordeum spp. | Panicum miliaceum |
| Secale spp. | Oryza spp. |
| Saccharum offinicarum | | and in dicotyledon crops such as

| | |
|---|---|
| Cruciferae, e.g. | |
| Brassica spp. | Raphanus spp. |
| Sinapis spp. | Lepidium spp. |
| Compositae, e.g. | |
| Lactuca spp. | Carthamus spp. |
| Helianthus spp. | Scorzonera spp. |
| Malvaceae, e.g. | |
| Gossypium hirsutum | |
| Leguminosae, e.g. | |
| Medicago spp. | Phaseolus spp. |
| Trifolium spp. | Arachis spp. |
| Pisum spp. | Glycine max. |
| Chenopodiaceae, e.g. | |
| Beta vulgaris | |
| Spinacia spp. | |
| Solanaceae, e.g. | |
| Solanum spp. | Capsicum annuum |
| Nicotiania spp. | |
| Linaceae, e.g. | |
| Petroselinum spp. | Apium graveolens |
| Daucus carota | |
| Rosaceae, e.g. | Fragaria |
| Cucurbitaceae, e.g. | |
| Cucumis spp. | Cucurbita spp. |
| Liliaceae, e.g. | |
| Linum spp. | |
| Umbelliferae, e.g. | |
| Allium spp. | |
| Vitaceae, e.g. | |
| Vitis vinifera | |
| Bromeliaceae, e.g. | |
| Ananas sativus. | |

EXAMPLE 2

In the greenhouse, loamy sandy soil was filled into pots and sown with various seeds. The soil was then immediately treated with 3 kg/ha of each of the following active ingredients, each being dispersed or emulsified in 500 liters of water per hectare:

I  O-(isopropylaminosulfonyl)-glycolic acid-N,N-diallylamide
II  O-(ethylaminosulfonyl)-glycolic acid-N,N-diallylamide
III  O-(n-propylaminosulfonyl)-glycolic acid-N,N-diallylamide
IV  O-(n-butylaminosulfonyl)-glycolic acid-N,N-diallylamide
V  O-(sec-butylaminosulfonyl)-glycolic acid-N,N-diallylamide
VI  O-(methylaminosulfonyl)-glycolic acid-N,N-diallylamide
VII  N,N-diallyl-2-chloroacetamide (comparative agent)
IX  O-(isopropylaminosulfonyl)-glycolic acid-N-butyn-1-yl-3-anilide (comparative agent).

After 4 to 5 weeks it was ascertained that compounds I to VI had better compatibility with the crop plants Brassica napus and Beta vulgaris than compound IX, and a better herbicidal action than compound VII.

The results are given below:

each compound being dispersed or emulsified in 500 liters of water per hectare.

After 2 to 3 weeks it was ascertained that active ingredients I to VI and VIII had better crop compatibility and a better herbicidal action than compound VII.

The results are given below:

| Active ingredient kg/ha | I 3.0 | II 3.0 | III 3.0 | IV 3.0 | V 3.0 | VI 3.0 | VII 3.0 | VIII 3.0 |
|---|---|---|---|---|---|---|---|---|
| Crop plants: | | | | | | | | |
| Brassica napus | 0 | 0 | 0 | 0 | 0 | 0 | 10 | 0 |
| Beta vulgaris | 0 | 0 | 0 | 0 | 0 | 0 | 20 | 0 |
| Unwanted plants: | | | | | | | | |
| Lolium perenne | 95 | 85 | 90 | 90 | 90 | 70 | 50 | 90 |
| Echinochloa crus galli | 85 | 80 | 80 | 90 | 80 | 70 | 60 | 100 |
| Avena fatua | 80 | 75 | 80 | 85 | 80 | 60 | 45 | 80 |

0 = no damage
100 = complete destruction

EXAMPLE 4

In the greenhouse, loamy sandy soil was filled into pots and sown with various seeds. The soil was then immediately treated with 2 kg/ha of VIII and VII (comparative agent), each compound being dispersed or emulsified in 500 liters of water per hectare.

After 4 to 5 weeks it was ascertained that active ingredient VIII had better crop plant compatibility and a better herbicidal action than compound VII.

The results are given below:

| Active ingredient kg/ha | VIII 2 | VII 2 |
|---|---|---|
| Crop plants: | | |
| Brassica napus | 0 | 5 |
| Beta vulgaris | 0 | 20 |
| Zea mays | 0 | 0 |
| Glycine max | 0 | 0 |
| Gossypium hirsutum | 0 | 0 |
| Hordeum vulgare | 5 | 20 |
| Triticum aestivum | 10 | 35 |
| Unwanted plants: | | |
| Lolium perenne | 95 | 70 |
| Echinochloa crus-galli | 95 | 65 |
| Avena fatua | 90 | 60 |

0 = no damage
100 = complete destruction

| Active ingredient kg/ha | I 3.0 | II 3.0 | III 3.0 | IV 3.0 | V 3.0 | VI 3.0 | VII 3.0 | IX 3.0 |
|---|---|---|---|---|---|---|---|---|
| Crop plants: | | | | | | | | |
| Brassica napus | 0 | 0 | 0 | 0 | 0 | 0 | 0 | 10 |
| Beta vulgaris | 0 | 0 | 0 | 0 | 0 | 0 | 30 | 5 |
| Zea mays | 0 | 0 | 0 | 0 | 0 | 0 | 0 | 40 |
| Soja hispida | 0 | 0 | 0 | 0 | 0 | 0 | 0 | 5 |
| Gossypium hirsutum | 0 | 0 | 0 | 0 | 0 | 0 | 0 | 10 |
| Unwanted plants: | | | | | | | | |
| Lolium perenne | 100 | 100 | 100 | 100 | 100 | 90 | 85 | 100 |
| Echinochloa crus-galli | 100 | 95 | 100 | 100 | 95 | 85 | 80 | 95 |
| Avena fatua | 80 | 80 | 100 | 100 | 95 | 70 | 70 | 80 |

0 = no damage
100 = complete destruction

EXAMPLE 3

In the greenhouse, various plants were treated at a growth height of from 8 to 16 cm with 3 kg/ha of each of compounds I to VII and VIII (O-(2-chloroethylaminosulfonyl)-glycolic acid-N,N-diallylamide),

EXAMPLE 5

In the greenhouse, various plants were treated at a growth height of from 6 to 8 cm with 6.0 kg/ha of each of the following compounds, each compund being emulsified or dispersed in 500 liters of water per hectare:

X O-(dimethylaminosulfonyl)-glycolic acid-N,N-diallylamide

XI O-(methylethylaminosulfonyl)-glycolic acid-N,N-diallylamide

XII O-(diethylaminosulfonyl)-glycolic acid-N,N-diallylamide.

During the experiment, 12 to 24 mm of precipitate was added to the plants, with the exception of Echinochloa crus-galli, which received 110 mm.

After 2 to 3 weeks it was ascertained that the active ingredients had a satisfactory to good herbicidal action, and good crop plant compatibility.

The results are given below:

| Active ingredient kg/ha | X 6.0 | XI 6.0 | XII 6.0 |
|---|---|---|---|
| Crop plant: | | | |
| Triticum aestivum | 0 | 0 | 0 |
| Unwanted plants: | | | |
| Echinochloa crus-galli | 80 | 88 | 90 |
| Alopercurus myosuroides | 70 | 78 | 60 |
| 0 = no damage | | | |
| 100 = complete destruction | | | |

EXAMPLE 6

In the greenhouse, loamy sandy soil was filled into pots and sown with various seeds. The soil was then immediately treated with 3.0 kg/ha of each of the following active ingredients, each being dispersed or emulsified in 500 liters of water per hectare:

X O-(dimethylaminosulfonyl)-glycolic acid-N,N-diallylamide

XI O-(methylethylaminosulfonyl)-glycolic acid-N,N-diallylamide

XII O-(diethylaminosulfonyl)-glycolic acid-N,N-diallylamide

XIII O-(methyl-2-chloroethylaminosulfonyl)-glycolic acid-N,N-diallylamide.

During the experiment, 15 to 25 mm of precipitate was added.

After 4 to 5 weeks it was ascertained that the active ingredients had a strong herbicidal action on Alopecurus myosuroides, combined with excellent compatibility with Sinapis alba.

The results are given below:

| Active ingredient kg/ha | X 3.0 | XI 3.0 | XII 3.0 | XIII 3.0 |
|---|---|---|---|---|
| Sinapis alba | 0 | 0 | 0 | 0 |
| Alopecurus myosuroides | 80 | 98 | 98 | 90 |
| 0 = no damage | | | | |
| 100 = complete destruction | | | | |

These results indicate the suitability of the active ingredients for controlling unwanted grasses in dicotyledonous crops.

EXAMPLE 7

In the greenhouse, various plants were treated at a growth height of from 2 to 7 cm with 0.8 and 1.0 kg/ha of active ingredient VIII, each amount being emulsified or dispersed in 500 liters of water per hectare.

During the experiment, 80 to 100 mm of precipitate was added.

After 3 to 4 weeks it was ascertained that the active ingredient had a good herbicidal action at the rate of 0.8 kg/ha, and excellent crop plant compatibility at the rate of 1.0 kg/ha.

The results are given below:

| Active ingredient kg/ha | VIII 0.8 | 1.0 |
|---|---|---|
| Crop plants: | | |
| Gossypium hirsutum | | 0 |
| Zea mays | | 0 |
| Unwanted plants: | | |
| Alopecurus myosuroides | 90 | |
| Digitaria sanguinalis | 100 | |
| Setaria faberii | 100 | |
| 0 = no damage | | |
| 100 = complete destruction | | |

EXAMPLE 8

90 parts by weight of compound I is mixed with 10 parts by weight of N-methyl-α-pyrrolidone. A mixture is obtained which is suitable for application in the form of very fine drops.

EXAMPLE 9

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound III is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound IV is dissolved in a mixture consisting of 25 parts by weight od cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of compound VI is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 13

3 parts by weight of compound I is intimately mixed with 97 parts by weight of particulate kaolin. A dust is obtained containing 3% by weight of the active ingredient.

EXAMPLE 14

30 parts by weight of compound II is intimately mixed with a mixture consisting of 92 parts by weight of powdered silica gel and 8 parts by weight of paraffin oil which has been sprayed onto the surface of this silica gel. a formulation of the active ingredient is obtained having good adherence.

We claim:

1. A substituted O-(aminosulfonyl)-glycolic amide of the formula

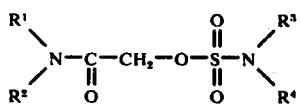

where $R^1$ is alkyl of 1 to 8 carbon atoms, alkenyl of 3 to 8 carbon atoms or alkynyl of 3 to 8 carbon atoms, $R^2$ is alkyl of 1 to 8 carbon atoms or alkenyl of 3 to 8 carbon atoms, $R^3$ is hydrogen, alkyl of 1 to 8 carbon atoms or halogen alkyl of 1 to 8 carbon atoms and $R^4$ is hydrogen, alkyl of 1 to 8 carbon atoms or haloalkyl of 1 to 8 carbon atoms.

2. O-(aminoslfonyl)-glycolic acid-N,N-diallylamide.
3. O-(methylaminosulfonyl)-glycolic acid-N,N-diallylamide.
4. O-(ethylaminosulfonyl)-glycolic acid-N,N-diallylamide.
5. O-(propylaminosulfonyl)-glycolic acid-N,N-diallylamide.
6. O-(isopropylaminosulfonyl)glycolic acid-N,N-diallylamide.
7. O-(n-butylaminosulfonyl)-glycolic acid-N,N-diallylamide.
8. O-(sec-butylaminosulfonyl)-glycolic acid-N,N-diallylamide.
9. O-(2-chloroethylaminosulfonyl)-glycolic acid-N,N-diallylamide.
10. O-(dimethylaminosulfonyl)-glycolic acid-N,N-diallylamide.
11. O-(methylethylaminosulfonyl)-glycolic acid-N,N-diallylamide.
12. O-(diethylaminosulfonyl)-glycolic acid-N,N-diallylamide.
13. O-(methyl-2-chloroethylaminosulfonyl)-glycolic acid-N,N-diallylamide.

* * * * *